United States Patent
Zurlo et al.

(10) Patent No.: US 11,028,125 B2
(45) Date of Patent: Jun. 8, 2021

(54) METHODS FOR EXTRACTING PROTEINS FROM A BLOOD-BASED MATERIAL

(71) Applicant: Plasma Technologies, LLC, Charleston, SC (US)

(72) Inventors: Eugene Zurlo, Charleston, SC (US); David Peter Nowotnik, Colleyville, TX (US); Charles Heldebrant, Arcadia, CA (US); Dennis Curtin, New York, NY (US)

(73) Assignee: Plasma Technologies, LLC, Charleston, SC (US)

( * ) Notice: Subject to any disclaimer, the term of this patent is extended or adjusted under 35 U.S.C. 154(b) by 0 days.

(21) Appl. No.: 16/072,175

(22) PCT Filed: Aug. 10, 2017

(86) PCT No.: PCT/US2017/016595
§ 371 (c)(1),
(2) Date: Jul. 23, 2018

(87) PCT Pub. No.: WO2017/136785
PCT Pub. Date: Aug. 10, 2017

(65) Prior Publication Data
US 2019/0055282 A1 Feb. 21, 2019

Related U.S. Application Data

(60) Provisional application No. 62/290,638, filed on Feb. 3, 2016.

(51) Int. Cl.
*C07K 1/36* (2006.01)
*C07K 1/22* (2006.01)
(Continued)

(52) U.S. Cl.
CPC ............ *C07K 1/36* (2013.01); *A61K 35/14* (2013.01); *A61K 38/36* (2013.01); *A61K 38/363* (2013.01);
(Continued)

(58) Field of Classification Search
CPC ...... G01N 33/491; G01N 30/04; G01N 30/06; G01N 2030/062; G01N 2030/065;
(Continued)

(56) References Cited

U.S. PATENT DOCUMENTS

| 2,390,074 A | 12/1945 | Cohn |
| 4,404,132 A | 9/1983 | Mitra |

(Continued)

FOREIGN PATENT DOCUMENTS

| EP | 0440483 A2 | 1/1991 |
| EP | 2823714 A1 | 1/2015 |

(Continued)

OTHER PUBLICATIONS

International Search Report and Written Opinion for PCT/US2017/016595, dated May 8, 2017, 17 pages.

*Primary Examiner* — Katherine Zalasky McDonald
(74) *Attorney, Agent, or Firm* — Fish IP Law, LLP

(57) ABSTRACT

Methods of producing multiple protein products from blood-based materials including alpha-1-proteinase inhibitor, gamma globulin, albumin, and other proteins are described herein. The inventive methods include steps of: salt fractionation, chromatography, ultrafiltration, diafiltration, solvent-detergent treatment, and sterile filtration. Advantageously, the inventive methods are simple and produce alpha-1-proteinase inhibitor, gamma globulin, albumin, and other proteins in high yields. The sequence of process steps can be selected to obtain multiple products from various (Continued)

in-process materials, such as supernatants, pastes, chromatography flow-though, and chromatography washes.

6 Claims, 11 Drawing Sheets

(51) Int. Cl.
| | | |
|---|---|---|
| *C07K 1/34* | (2006.01) | |
| *C07K 1/16* | (2006.01) | |
| *C07K 1/30* | (2006.01) | |
| *B01D 15/36* | (2006.01) | |
| *B01D 61/02* | (2006.01) | |
| *B01D 61/14* | (2006.01) | |
| *C07K 14/81* | (2006.01) | |
| *C07K 16/06* | (2006.01) | |
| *A61K 38/48* | (2006.01) | |
| *A61K 38/36* | (2006.01) | |
| *A61K 35/14* | (2015.01) | |
| *A61K 38/38* | (2006.01) | |
| *A61K 38/37* | (2006.01) | |
| *A61K 38/57* | (2006.01) | |
| *B01D 15/38* | (2006.01) | |

(52) U.S. Cl.
CPC .............. *A61K 38/37* (2013.01); *A61K 38/38* (2013.01); *A61K 38/4846* (2013.01); *A61K 38/57* (2013.01); *B01D 15/361* (2013.01); *B01D 15/3814* (2013.01); *B01D 61/027* (2013.01); *B01D 61/145* (2013.01); *C07K 1/16* (2013.01); *C07K 1/22* (2013.01); *C07K 1/30* (2013.01); *C07K 1/34* (2013.01); *C07K 14/81* (2013.01); *C07K 16/06* (2013.01); *B01D 2315/16* (2013.01)

(58) Field of Classification Search
CPC ........ G01N 2030/14; G01N 1/28; G01N 1/40; G01N 1/4055; G01N 1/34; G01N 2001/4061; G01N 2001/4066; G01N 2001/4088; G01N 2001/4083; B01D 15/38; B01D 15/3804; B01D 15/3809; B01D 15/3823; B01D 15/12; B01D 15/125; B01D 11/04; B01D 11/0492; C07K 1/18; C07K 1/122; C07K 1/32; C07K 1/303; C07K 1/30; C07K 1/34; C07K 1/36; C07K 14/8125; C07K 14/8128; C07K 16/00
See application file for complete search history.

(56) References Cited

U.S. PATENT DOCUMENTS

| | | | |
|---|---|---|---|
| 4,486,282 | A | 12/1984 | Bier |
| 4,639,513 | A * | 1/1987 | Hou .................... B01J 20/3217 424/177.1 |
| 4,697,003 | A | 9/1987 | Coan |
| 5,177,194 | A | 1/1993 | Samo et al. |
| 6,402,913 | B1 | 6/2002 | Gilbert et al. |
| 6,485,932 | B1 | 11/2002 | McIntosh et al. |
| 6,541,518 | B2 | 4/2003 | Shanbrom |
| 6,835,379 | B2 * | 12/2004 | Andersson .......... C07K 16/065 424/130.1 |
| 6,955,917 | B2 | 10/2005 | Alred et al. |
| 7,297,716 | B2 | 11/2007 | Shanbrom |
| 7,879,331 | B2 | 2/2011 | Zurlo et al. |
| 7,879,332 | B2 | 2/2011 | Zurlo et al. |
| 8,063,189 | B2 | 11/2011 | Arunakumari et al. |
| 8,293,242 | B2 | 10/2012 | Zurlo et al. |
| 2002/0151688 | A1 | 10/2002 | Ristol Debart et al. |
| 2003/0022149 | A1 | 1/2003 | Shanbrom |
| 2003/0129167 | A1 | 7/2003 | Shanbrom |
| 2007/0049732 | A1 | 3/2007 | Zurlo et al. |
| 2007/0049734 | A1 * | 3/2007 | Zurlo ................. A61M 1/3693 530/387.1 |
| 2009/0292114 | A1 | 11/2009 | Kumpalume et al. |
| 2011/0152503 | A1 | 6/2011 | Zurlo et al. |
| 2011/0237781 | A1 | 9/2011 | Lebing et al. |
| 2014/0343253 | A1 | 11/2014 | Van Alstine et al. |
| 2018/0306772 | A1 * | 10/2018 | Zurlo .................... C07K 14/81 |

FOREIGN PATENT DOCUMENTS

| | | |
|---|---|---|
| WO | WO02087560 A1 | 11/2002 |
| WO | WO2017136785 A1 | 8/2017 |

* cited by examiner

Example processes constructed from process modules:

A

B

C

METHODS FOR EXTRACTING PROTEINS FROM A BLOOD-BASED MATERIAL

This application claims the benefit of priority to U.S. Provisional Patent Application No. 62/290,638, filed Feb. 3, 2016.

FIELD OF THE INVENTION

The field of the invention is improved methods for increasing the purity and yields of multiple protein products, such as alpha-1-proteinase inhibitor (also known as alpha-1 antitrypsin), albumin, immunoglobulin (also referred to as immune globulin), and other protein products.

BACKGROUND

The following background discussion includes information that may be useful in understanding the present invention. It is not an admission that any of the information provided herein is prior art or relevant to the presently claimed invention, or that any publication specifically or implicitly referenced is prior art.

U.S. Pat. No. 7,297,716 to Shanbrom discloses methods of isolating blood products (e.g., fibrin glue) from cryoprecipitate. Shanbrom's methods use salts to increase the yield of cryoprecipitate. For example, 2-10 weight percent ("wt %") sodium citrate is added to blood or plasma. Sodium citrate at this concentration inactivates and/or inhibits pathogenic microorganisms, prevents cells and proteins from denaturing, increases the yield of cryoprecipitate (even without freezing), and facilitates the removal of denatured components. From the cryoprecipitate poor plasma, Shanbrom contemplates isolation of various clotting factors including fibrinogen, factor II, factor V, factor VII, factor VIII, factor IX, factor X, and platelets. However, Shanbrom fails to appreciate that salts can be added to previously frozen blood products to concentrations above 11 wt %. Moreover, Shanbrom further fails to appreciate that protein products can be extracted from any supernatant, including the supernatants formed from multiple salt fractionation steps that give intermediates having 11-13%, 21-23 wt %, and even 50 wt % salt.

In U.S. Pat. Nos. 7,879,331; 7,879,332; and 8,293,242, the inventors conceived of a salting procedure that eliminates the use of ethanol in extracting and preparing protein products from blood products. Ethanol and other alcohols can be problematic because they tend to denature the desirable proteins.

In the current inventive subject matter, the inventors discovered simplified methods in which cryoprecipitate need not be separated from the cryoprecipitate poor plasma (cryo-poor plasma) before the salt precipitation steps. Additionally, other blood products, including in-process materials, can be employed as the substrate for salt fractionation leading to isolation of purified proteins. Also, in cases when very little desired protein product remains in the first and second pastes, high yields of the desired protein product can be maintained without re-dissolving the pastes and conducting further purification steps. In the case of alpha-1-proteinase inhibitor, the inventors discovered that very little alpha-1-proteinase inhibitor precipitates at a salt concentrations from 22 wt % to as high as 34 wt %. This result is surprising in view of literature that teaches alpha-1-proteinase inhibitor precipitates at high salt concentrations. Because very little alpha-1-proteinase inhibitor is lost in pastes, and high yields can be obtained from the second supernatant. Thus, the processes are improved by elimination of the paste processing. Processes contemplated herein include those which involve only a single salt fractionation step, diafiltration, and a single purification step (e.g., chromatography) or multiples of these steps as required to provide purified proteins.

Surprisingly, the second supernatant can be applied to an affinity column with minimal pre-processing (e.g., bioburden filtration, solvent/detergent treatment, diafiltration, or ultrafiltration), further simplifying the isolation of protein products. Moreover, additional protein products such as albumin and immunoglobulin can be obtained from various process intermediates.

These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

SUMMARY OF THE INVENTION

The inventive subject matter provides methods in which one can produce a protein product from a blood-based material. Preferred methods include steps of (1) adding a salt to the blood-based material to produce a first intermediate, wherein the salt comprises between 11-20 wt % of the first intermediate; (2) separating the first intermediate to produce a first supernatant and a first paste; (3) adding a salt to the first supernatant to produce a second intermediate, wherein the salt comprises between 15-30 wt % of the second intermediate; (4) separating the second intermediate to produce a second supernatant and a second paste; (5) separating a third intermediate from the second supernatant by a suitable chromatographic method (e.g., affinity chromatography; and (6) separating the third intermediate by a suitable chromatographic method (e.g., ion exchange chromatography to produce an eluate containing the protein product. The combination of steps (1) and (2) or the combination of steps (3) and (4) are sometimes referred to throughout this document as "salt fractionation." It is within the scope of the inventive subject matter, especially when the blood-based material has undergone prior processing, that a single salt fraction step produces the desired protein and/or a single chromatographic step yields the desired protein with acceptable purity. While protein purification by chromatography is preferred, other methods of protein purification known in the art can be incorporated in the inventive methods in lieu of or in addition to chromatography to isolate one or more desired proteins from the intermediates obtained by salt fractionation.

It is contemplated that several types of proteins can be selectively extracted from a single lot of blood-based material. It should be appreciated that each of the first paste, the second paste, any paste generated according to the inventive subject matter in this document, a flow-through from a first chromatography purification step (e.g., an affinity chromatography run), a flow-through from a second chromatography purification step (e.g., ion exchange chromatography), any fraction from any chromatography run performed according to inventive subject matter disclosed in this document, and other in-process materials of the inventive subject matter can be further processed by salt fractionation and/or chromatography. As used herein, "in-process material" refers to materials produced by individual process steps. In preferred embodiments, the further processing of the above referenced material produces an isolated protein from the blood-based material. It is also contemplated that in-process material of the inventive subject matter be used as a starting point for other fractionation and/or purification processes (e.g., ProMetic Life Sciences Incorporated processes including the Plasma Protein Purification Scheme, Therapure Biopharma Incorporated processes including the PlasmaCap EBA process, and/or other known fractionation processes).

As used herein, "blood-based material" is defined as blood plasma, Source Plasma, fresh frozen plasma, Recovered Plasma, salvaged plasma, fractionated blood plasma, Cohn fractions, Nitschmann and Kistler fractions, and in-process materials. It should be appreciated that although the methods described herein do not necessarily require a frozen plasma containing product as a starting material, conventional plasma containing products are typically frozen, and a thawing step is usually required before further processing and/or purification.

With respect to the salt added to the blood-based material, there is a wide range of salts that can be used, including for example (without limitation), citrates, acetates, gluconates, and/or caprylates. Suitable salts are water-soluble. Although use of water-soluble salts is preferred, use of water-insoluble salts (e.g., calcium citrate and/or other salts with low solubility in water) with chelating agents (e.g., EDTA) that improve the solubility of insoluble salts is not excluded. Typically a first precipitate and a first supernatant form in first intermediates having salt contents of between 10.1-25 wt %, more typically, 10.1-11, 11-13, 13-15, and 15-20 wt %. Protein separation might be improved by pH adjustment to a specific value in the range 3-10 and/or by adjusting the temperature of the mixture to a specific value in the range 0-25° C.

In some embodiments reducing agents that stabilize proteins (e.g., minimize multimer formation) are added to the blood-based material, the first intermediate, the first supernatant, the first paste, the second intermediate, the second supernatant, or the second paste, and/or any combination thereof (e.g., tris(2-carboxyethyl)phosphine ("TCEP"), Dithiothreitol ("DTT"), β-mercaptoethanol ("βME") and/or salts thereof). Other practical protein purification and/or stabilization methods known in the art may also be used as intermittent steps of the inventive subject matter.

It should be appreciated that the step of separating the first intermediate to produce a first supernatant and a first paste can be achieved by centrifugation and/or filtration. When centrifugation is used, the first precipitate forms a pellet (i.e., the first paste) from which the first supernatant can be decanted, pipetted, or otherwise removed. The pellet is also referred to herein as paste. At larger process scales, filtration is preferable to centrifugation. When filtration is used, the first supernatant is the filtrate and the first precipitate forms the filter cake (i.e., the first paste/precipitate). The terms paste and precipitate are used interchangeably in this document, pastes typically obtained by (for example) centrifugation for the separation of precipitate from supernatant.

In regard to the second supernatant, typical salt contents of between 15 and 50 wt % more typically 15-21, 21-23, 23-25, 25-27, 27-30, 30-33, 33-37, 37-40, 40-43, 43-47, and 47-50 wt % are contemplated. Because salt is added to the first supernatant, the salt concentration of the second intermediate will be greater than the salt concentration of the first intermediate. Protein separation might be improved by pH adjustment to a specific value in the range 3-10 and/or by adjusting the temperature of the mixture to a specific value in the range 0-25° C. The same considerations apply to the separation of the second supernatant from the second precipitate as applied to the separation of the first supernatant and the first precipitate. In processes involving a single salt fractionation step, typical salt contents of between 15 and 50 wt % can be used as described above. It is also contemplated that salt fractionation can be performed on the redissolved second paste wherein the salt concentration can be either less than or greater than the salt concentration of the first slat fraction step.

It is contemplated that blood-material can be processed first by chromatography to produce a first flow-through and a first eluate, as depicted in FIG. 6. It should be appreciated that chromatography can produce more than one distinct eluate and that each eluate can be independently processed to yield the same or different proteins. Salt is then added to the first flow-through in the manner described throughout this document creating a first intermediate. The first intermediate is separated into a first supernatant and a first paste. As described throughout this document, it is contemplated that a single chromatography process can be used (e.g., affinity chromatography), a series of the same chromatography process in sequence can be used (e.g., two ion exchange chromatography runs in sequence), a series of the same chromatography process with intermediate processes can be used (e.g., an ion exchange chromatography run followed by salt fractionation followed by an ion exchange chromatography run), a series of different chromatography processes in sequence can be used (e.g., an affinity chromatography run followed by an ion exchange chromatography run), a series of the different chromatography processes with intermediate processes can be used (e.g., an affinity chromatography run followed by salt fractionation followed by an ion exchange chromatography run), or a combination of any of these schemes can be used. It should be appreciated that while affinity and ion exchange chromatography are preferred, the inventive subject matter contemplates blood-based material processed by gel permeation, size exclusion, cation exchange, anion exchange, hydrophobic interaction, hydroxyapatite, fluoroapatite, expanded bed absorption, or immobilized metal ion affinity chromatography.

As used herein, diafiltration means continuous filtration used to exchange the solution/buffer containing the protein product. Ultrafiltration, as used herein is a continuous filtration process that concentrates a dilute solution of the protein product. For diafiltration and ultrafiltration, both perpendicular and tangential flow configurations are contemplated. Advantageously, diafiltration and/or ultrafiltration remove salt, low molecular weight species, and/or processing agents. It should be appreciated that diafiltration or ultrafiltration can be used between salt fractionation steps and/or chromatography steps, and/or between a salt fractionation step and a chromatography step of the inventive subject matter. In some embodiments of the inventive methods, prior to subjecting a supernatant or redissolved paste to affinity chromatography, the supernatant or redissolved paste can be filtered to remove bioburden, treated with a solvent and a detergent to inactivate any enveloped viruses in the supernatant/redissolved paste, and/or desalted (e.g., by diafiltration and/or ultrafiltration).

In some exemplary embodiments, an appropriate affinity resin is used in the step of separating an intermediate from a supernatant or redissolved paste by affinity chromatography. Affinity resins can be purchased from suppliers such as Bio-Rad, Sigma-Aldrich, GE Healthcare Life Sciences, Thermo Fisher Scientific, Merck Millipore, GenScript, and ProMetic Life Sciences.

In one process used in the production of alpha-1-proteinase inhibitor, for example, an alpha-1-proteinase inhibitor specific affinity resin is used to produce a third intermediate that contains alpha-1-proteinase inhibitor. Similarly, an albumin specific affinity resin can be used to isolate albumin from the second supernatant. Therefore, it should be apparent that the second supernatant can be applied to numerous affinity chromatography columns in series to extract different proteins. For example, the affinity chromatography step in the production of alpha-1-proteinase inhibitor produces a flow-through and a wash. The flow-through and/or wash can be applied to an albumin-specific affinity column. The flow-through and/or wash from the albumin specific affinity column can then be applied to a third affinity column specific to the same or a different protein.

To inactivate and/or remove viruses from the protein product, the eluate can be treated with solvent detergent, nano-filtered, pasteurized or otherwise treated with a method shown to inactivate or remove viruses. Methods according to the inventive subject matter are especially suitable for the preparation of protein products including alpha-1-proteinase inhibitor, gamma globulin, albumin, and/or other proteins.

In other aspects, the inventive methods may further comprise isolating a second protein product from the first paste or the second paste. Additionally, a second protein product may be isolated from a flow-through and/or a wash produced in the course of the affinity chromatography step. Therefore, it should be apparent that the second protein product can be different from the first protein product and may comprise alpha-1-proteinase inhibitor, gamma globulin, albumin, and/or other proteins.

In yet further aspects of the inventive subject matter, methods of producing gamma globulin may further comprise isolating gamma globulin from the second paste. Therefore, an IgG specific affinity resin can be used to isolate IgG from the second paste. Additionally, another affinity resin can be used to isolate a desired protein from a specific intermediate (e.g., including supernatants, precipitates (pastes), and chromatography fractions).

In some aspects, the inventive subject matter contemplates methods of producing products from blood-based materials comprising process modules, wherein each module can receive an input material and produces at least one output material. Each module can comprise a fractionation module, a chromatography module, a diafiltration module, or an ultrafiltration module. The type of modules can be configured in a variety of sequences to produce a variety of protein products from blood-based material. Some embodiments comprise two modules, but methods of the inventive subject matter can include three, four, or five modules, or as many modules as necessary to produce the desired product. Minimally, a process will contain a salt fractionation module and a diafiltration/ultrafiltration module.

Fractionation modules can convert input materials into a supernatant and a paste using salt fractionation, Cohn fractionation, Nitschmann and Kistler fractionation, caprylate fractionation, polyethylene glycol fractionation, or variations thereof. Suitable input materials include, blood-based materials, fractionated plasma, chromatography flow-through, eluate, wash, or sub-fractions thereof. One or more fractionation modules can also comprise salt fractionation steps as discussed herein, and produce at least a supernatant and a paste.

Contemplated chromatography modules employ processes, such as affinity chromatography, gel permeation, cation exchange, anion exchange, hydrophobic interaction, hydroxyapatite, fluoroapatite, expanded bed absorption, or immobilized metal ion affinity chromatography. It should be appreciated that chromatography modules separate input materials into flow-through, eluate, wash, and sub-fractions thereof. It is further contemplated that the input material for each module comprises the blood-based material, or comprises the flow-through, eluate, supernatant, or paste of any other module.

Various objects, features, aspects and advantages of the inventive subject matter will become more apparent from the following detailed description of preferred embodiments, along with the accompanying drawing figures in which like numerals represent like components.

DETAILED DESCRIPTION

The inventive subject matter provides improved methods of producing multiple protein products in high yields from a blood plasma containing product. Blood plasma contains numerous proteins and clotting factors that are useful therapeutics. For example, alpha-1-proteinase inhibitor is used to treat people with alpha-1-proteinase inhibitor deficiency, which can cause a breakdown in lung tissue. Another class of plasma proteins is gamma globulins, which are used to treat immune deficiencies and disorders. Albumin and other proteins (e.g., fibrinogen, prothrombin, alpha-1-acid glycoprotein, alpha-1-fetoprotein, alpha-2-macroblobulin, beta-2-microglobulin, haptoglobin, ceruloplasmin, complement component 3, complement component 4, C-reactive protein, transferrin, mannose-binding lectin, etc.) can also be isolated from plasma by methods according to the inventive subject matter.

In preferred embodiments, the blood-based material comprises Recovered Plasma or salvaged plasma, and more preferably fresh frozen plasma, and even more preferably Source Plasma. Other blood-based materials may be used, for example fractionated blood, fractionated blood-based material, fractionated plasma, caprylate-fractionated plasma, polyethylene glycol-fractionated plasma, Cohn fractions, Nitschmann and Kistler fractions, and any in-process material, or other material obtained by plasma fractionation. It should be appreciated that blood plasma containing products are typically stored and transported in a frozen state, and are thawed before further processing or purification. In the thawing process, the plasma may separate into a cryoprecipitate and "cryo-poor" plasma, the cryoprecipitate-poor plasma. As used herein "cryo-poor" plasma refers to the liquid supernatant that results from thawing frozen plasma and separating the cryoprecipitate from the plasma and does not include the cryoprecipitate. Preferably the whole plasma, i.e., both the cryo-poor plasma and the cryoprecipitate, is carried through further processing steps, although use of only the cryo-poor plasma in subsequent processing steps is not excluded. Optionally, the cryoprecipitate can be reincorporated (e.g., by mixing) in the cryo-poor plasma prior to or as part of protein product production.

Figure 1:
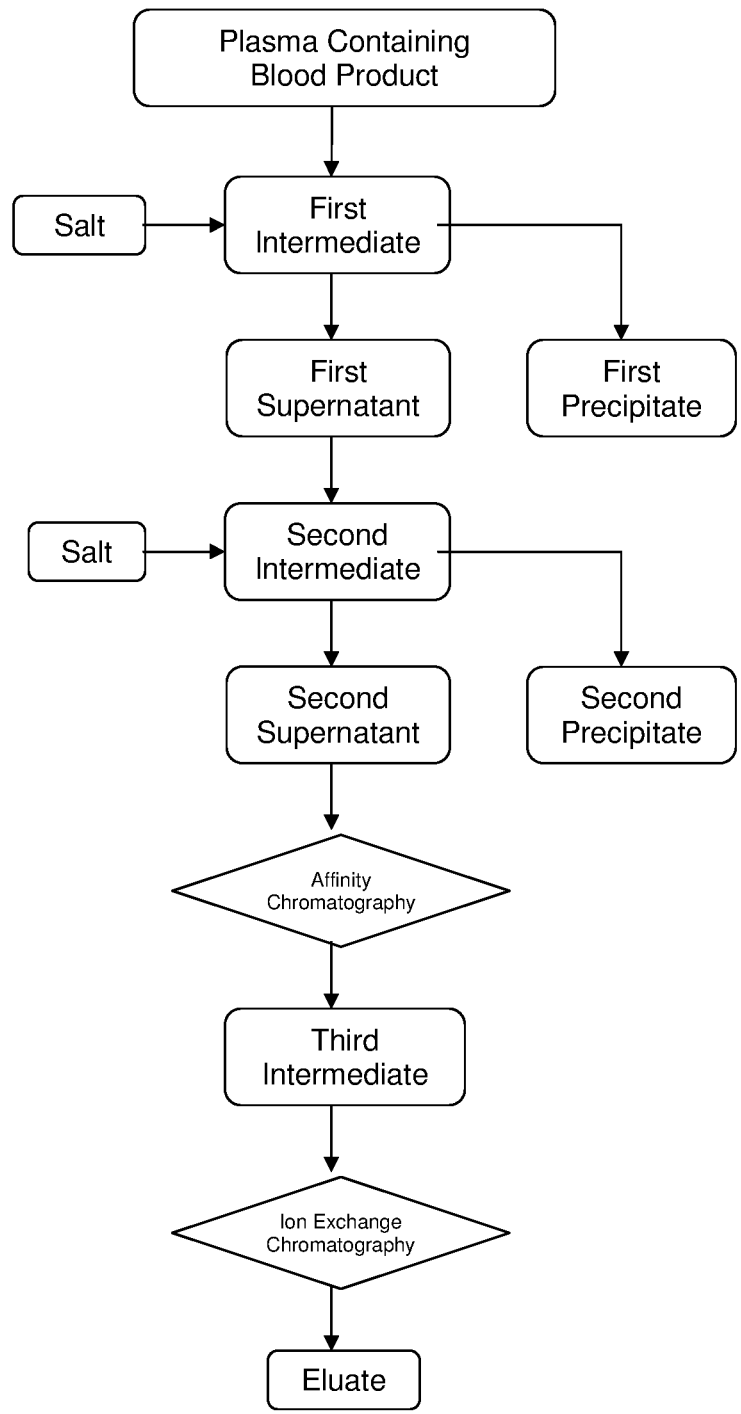
FIG. 1 is a schematic of a method of producing a protein product from a plasma-containing blood product.

In FIG. 1 a flow diagram of one embodiment of the inventive subject matter is shown. A fresh or thawed blood plasma containing product and a salt are mixed, forming the first intermediate that is typically 10.1-25 wt % added salt, more typically 10.1-11, 11-13, 13-15, and 15-20 wt % added salt, preferably, 11-13 wt %, and more preferably 12 wt % the added salt. A typical tolerance for salt concentrations is ±1 wt %. Suitable salts for use in the inventive methods include, but are not limited to citrates, acetates, gluconates, and caprylates. Although solid salt can be added to the blood plasma product, in preferred methods concentrated, pH-adjusted salt solutions are added to the blood plasma product. Depending on the desired protein product, the pH of the salt solutions can be adjusted from about pH 3 to pH 8 to optimize protein fractionation.

For example, a 50 wt % citric acid stock solution can be prepared by dissolving 500 g of citric acid in 600 mL of water (e.g., water for injection). The volume of the solution is then brought up to 1000 mL with additional water. A 50% sodium citrate solution can be prepared by dissolving 500 g of tri-sodium citrate in 600 mL of water. Enough citric acid solution is added to the sodium citrate solution to obtain a solution having a pH of about 7, and then enough water is added to bring the volume to 1000 mL.

The plasma, intermediates, and supernatants can be processed at temperatures between the freezing point of the solution and ambient temperature, generally between 0 and 25° C. In one embodiment, the blood plasma product is maintained at 20° C. and room temperature citric acid/citrate solution is added to the plasma until the citric acid/citrate comprises 11-13 wt %, and preferably 12% by weight of the first intermediate so obtained. The addition of the salt will cause the first intermediate to separate into a first precipitate and a first supernatant. In another embodiment, the first intermediate is stirred and cooled to between 2-8° C. generating a precipitate. The first precipitate contains high molecular weight proteins and most lipids. Preferably, the first intermediate is stirred until precipitation is complete (typically for 60 minutes or more).

The first supernatant and the first precipitate can be separated into the first supernatant and the first paste by centrifugation or filtration as described above. The first paste can then be dissolved and subjected to further processes, such as salt fractionation, chromatography processes, other conventional protein purification methods, or combinations thereof, as discussed in this document.

In an exemplary embodiment, the first supernatant is cooled to 2-8° C., and additional citric acid/citrate solution is added to the first supernatant producing the second intermediate, which comprises 15-21, 21-23, 23-25, 25-27, and 27-30 wt % citric acid/citrate, preferably 21-23 wt % citric acid/citrate, and more preferably 22 wt % citric acid/citrate. Use of salt/buffer combinations other than citric acid/citrate is also contemplated. One having ordinary skill in the art appreciates that the concentration of salt in the second intermediate is greater than the concentration of salt in the first intermediate. Preferably, the second intermediate is stirred until formation of the second precipitate is complete, for example, overnight Immune globulins can be found in the second precipitate.

Like the first intermediate, the second intermediate can be separated into a second supernatant and a second paste by centrifugation and/or filtration. When centrifugation is used, the second paste is the pellet formed from the second precipitate, and the second supernatant can be decanted, pipetted, or otherwise removed from the pellet. When filtration is used, the second paste is the filter cake formed by the second precipitate, and the second supernatant is the filtrate.

The eluate of the ion exchange chromatography preferably comprises one or more blood plasma proteins. In some embodiments, the eluate comprises one of alpha-1-proteinase inhibitor, a gamma globulin, albumin, fibrinogen, prothrombin, alpha-1-acid glycoprotein, alpha-1-fetoprotein, alpha-2-macroblobulin, beta-2-microglobulin, haptoglobin, ceruloplasmin, complement component 3, complement component 4, C-reactive protein, transferrin, and mannose-binding lectin. In some embodiments, the eluate comprises a combination of at least two of the above proteins.

Figure 2:
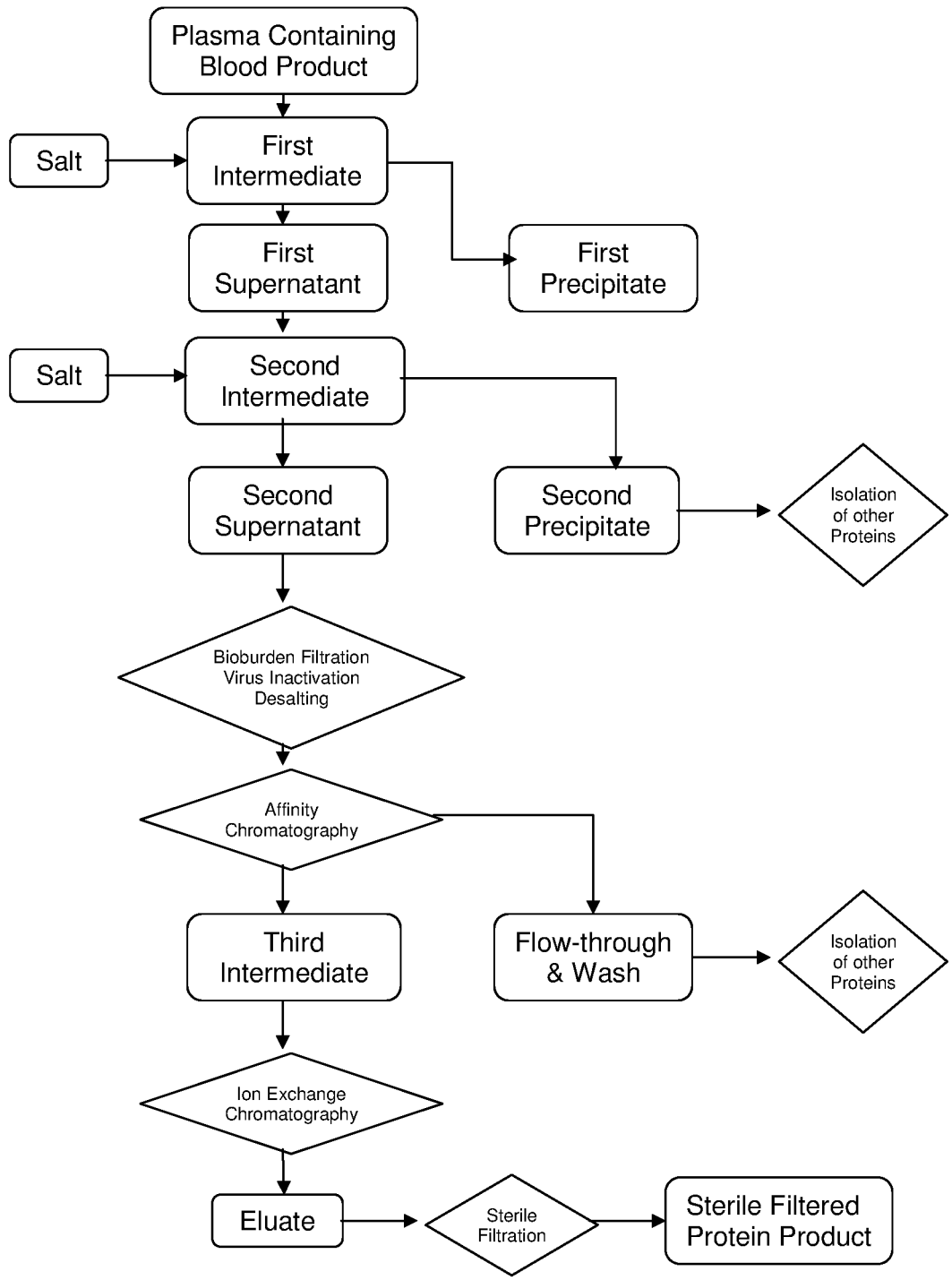
FIG. 2 is a schematic of another method of producing a protein product from a plasma-containing blood product.

Optionally, as shown in FIG. 2, the second supernatant can be filtered to remove bacteria, fungal spores, hyphae, and other "bioburden" using bioburden reduction filters. Exemplary bioburden reduction filters include filters made under the Sartorius, Pall, and EMD Millipore brands (e.g., Sartopore 2XLG 0.8/0.2, Supra EK1P/EAV1.5/0.2, Milligard®, Polysep® II, Lifegard™, Clarigard®, Polygard®-CN, Polygard®-CR, Polygard®-CT).

Another optional step is to reduce the citrate concentration by diafiltration and/or ultrafiltration. The size of the filter can be selected to maximize flow rate (e.g., 3-6 L/h) while preventing the protein of interest from flowing through the filter with the filtrate. For example 30 kD membranes retain alpha-1-proteinase inhibitor but allow relatively fast flow of the liquid through the membrane. Reduction in citrate concentration can be correlated with a reduction in conductivity from about 55-60 mS/cm to about 10 mS/cm, and most preferably to 5 mS/cm or less.

Inactivation of enveloped viruses and some non-enveloped viruses can be achieved by denaturing the viral envelope membrane lipids. For example, a solvent/detergent (e.g., tri-n-butyl phosphate and polysorbate 80; tri-n-butyl phosphate and Triton X-100) can be used to treat the second supernatant. Advantageously, solvent/detergent treatment may also kill bacterial and fungal contamination and wash away endotoxins. In a preferred embodiment of the inventive subject matter, 13.2 g of a 23.09:76.91 mixture of tri-n-butyl phosphate and polysorbate 80 per kg of the second supernatant is added to the second supernatant.

The inventors contemplated that affinity resins could be used to isolate individual components of protein products. As examples, ProMetic BioSciences Ltd. and ProMetic BioTherapeutics produces affinity resins that specifically bind coagulating factors, plasminogen, fibrinogen, immune globulins, albumin, alpha-1-proteinase inhibitor. GE Healthcare produces a cross-linked agarose resin bearing a single-domain antibody that binds alpha-1-proteinase inhibitor. The amount of resin required depends on the amount of protein in the second supernatant and the loading capacity of the resin. Typically after application of the second supernatant, the affinity resin is washed with a salt solution (e.g., 100 mM NaCl) that removes proteins adsorbed to the resin by non-specific electrostatic interactions. The desired protein is then eluted from the affinity column using an eluate recommended by the resin manufacturer, although use of other elution protocols are not excluded. In the case of alpha-1-proteinase inhibitor and the GE Healthcare Alpha-1 Antitrypsin Select resin, the protein product can be eluted from the affinity chromatography column using a buffered magnesium chloride solution (e.g., 2 M $MgCl_2$ in 50 mM Tris-HCl, pH=7.40). Typical protein product yields after the affinity chromatography step range between 70-98%.

The third intermediate is typically subjected to diafiltration/ultrafiltration to reduce the salt concentration. After diafiltration/ultrafiltration, the conductivity decreases from about 120 mS/cm to less than 10 mS/cm, and preferably 5 mS/cm or less.

The inventors expect that any affinity ligand that leaches from the resin into the third intermediate can be separated from the protein product after an ion exchange chromatography step. Suitable resins are supplied by Bio-Rad, Sigma-Aldrich, and Asahi Chemical & Industrial Co. Ltd. (e.g., Asahi Q500 anion exchange resin has exhibited a dynamic binding capacity of 26.5 mg of alpha-1-proteinase inhibitor per milliliter of resin). In contemplated methods, a 500 ml column of Q500 resin is equilibrated in 50 mM Tris-HCl, pH 7.40. The third intermediate is loaded on the column and eluted with a step gradient from 0 mM to 350 mM NaCl in 50 mM Tris-HCl, pH 7.40 buffer.

The inventive methods can further comprise a step of nano-filtration, which removes small non-enveloped viruses (e.g., Adenovirus, Parvovirus, papovaviruses, Human papillomaviruses) using a 20 nm pore filter. The nano-filtered protein product can then be further processed depending on the desired formulation. Further processing steps include one or more of ultrafiltration and/or diafiltration, formulation, a sterile filtration, filling, and lyophilization.

As depicted in FIG. 2, the flow-through, wash, and second precipitate each may contain one or a combination of the blood plasma proteins referenced herein. In preferred embodiments, the sterile filtered protein product of FIG. 2 comprises a single type of blood plasma protein. As depicted in FIG. 2, the isolation of other proteins from the second precipitate and the flow-through and wash comprises salt fractionation and chromatography processes as described herein.

Figure 3:
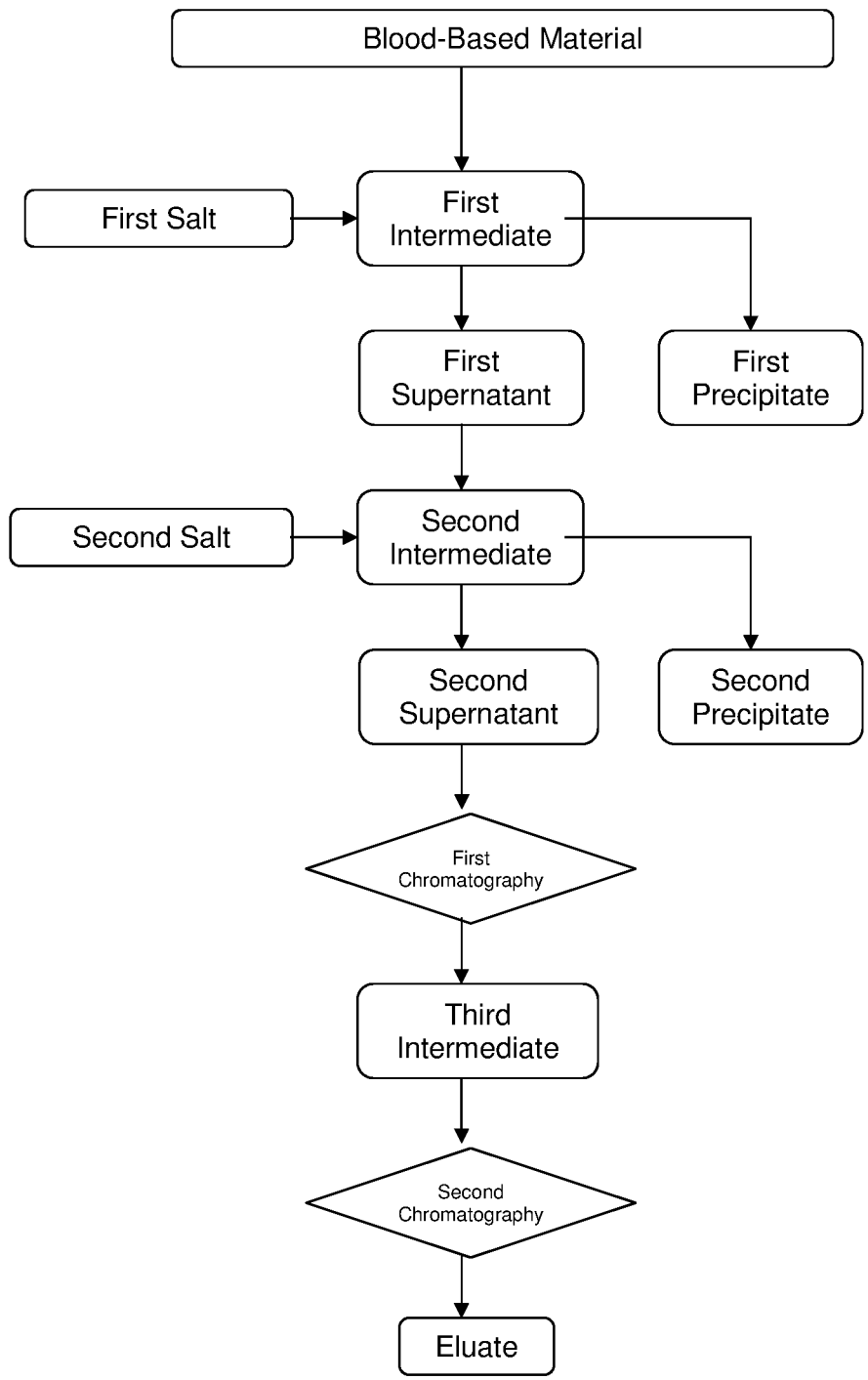
FIG. 3 is a schematic of another method of producing a protein product from a blood-based material.

FIG. 3 depicts a flow diagram similar to FIG. 1. However, the starting material in FIG. 3 is blood-based material. As described in this document, blood-based material includes Source Plasma, fresh frozen plasma, Recovered Plasma, salvaged plasma, fractionated blood, fractionated blood-based material, fractionated plasma, Cohn fractions, Nitschmann and Kistler fractions, and any in-process material of fractionated material. It is contemplated by the in-process materials from other fractionation processes, such as Cohn fractions or Nitschmann and Kistler fractions, can be used as a starting material for the method of FIG. 3. Further, it is anticipated that in-process material from any of the methods of the inventive subject matter, including at least FIGS. 1-8, can be used as a starting point for the method of FIG. 3.

It should be noted that the first salt and the second salt of FIG. 3 can be any of the salts disclosed in this document. Further, it is contemplated that first and second salts can be the same. The flow diagram of FIG. 3 also comprises first and second chromatography steps. It is contemplated that first and second chromatography steps can comprise, at least partially, affinity, gel permeation, cation exchange, anion exchange, size exclusion, hydrophobic interaction, hydroxyapatite, fluorapatite, or immobilized metal ion affinity chromatography. The first and second chromatographic steps can be in either packed bed or expanded bed adsorption mode. First and second chromatography steps can also comprise the same types of chromatography. It is contemplated that some processes may require a single chromatographic step while others may require more than two steps. If is further contemplated that protein purification from the protein fractions obtained using salts as described herein may require protein purification/stabilization steps in addition to chromatography or may require protein purification/stabilization steps other than chromatography.

As described above, it should be appreciated that the eluate from second chromatography process comprises at least one of the blood plasma proteins referenced herein.

Figure 4:
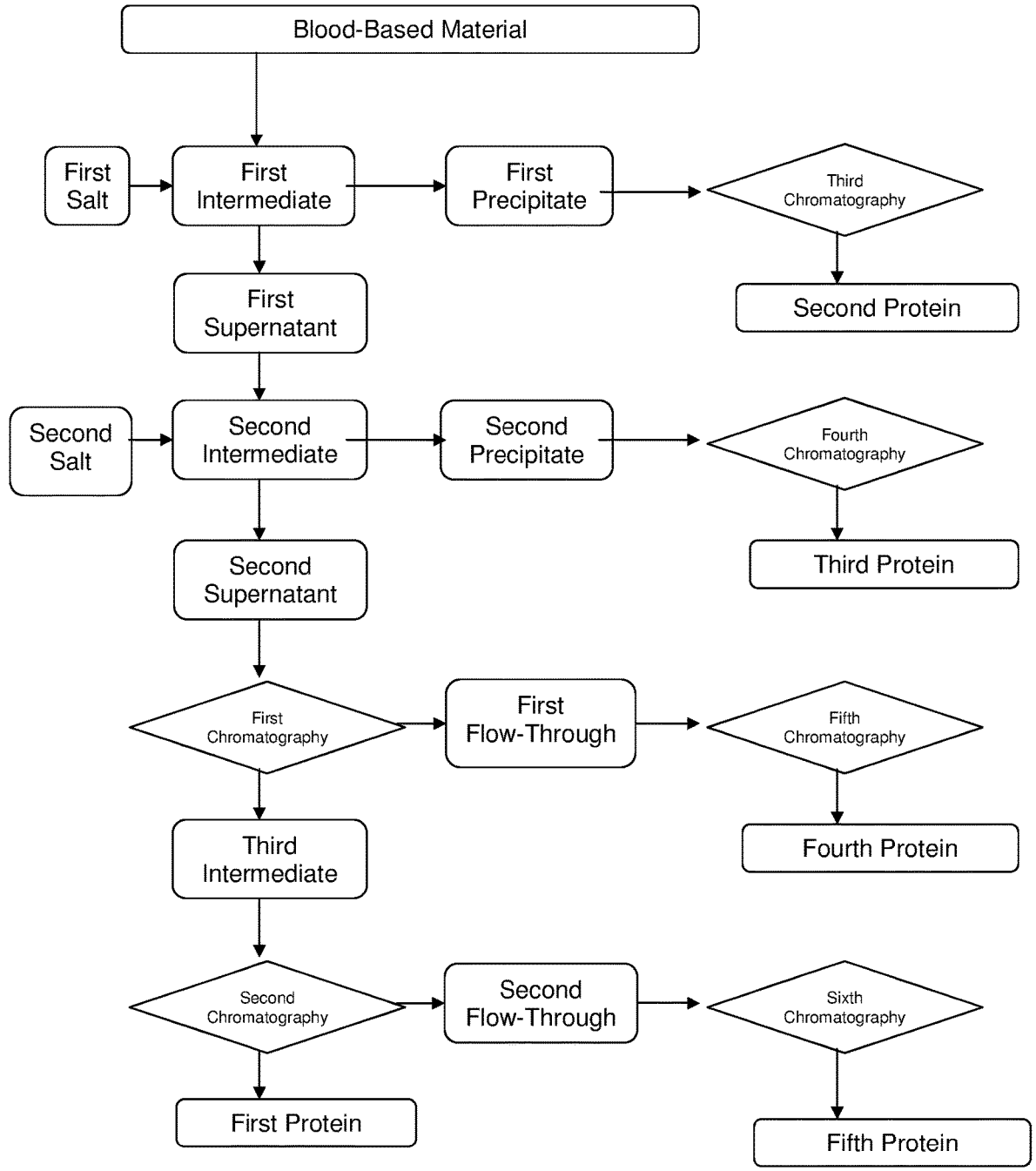
FIG. 4 is a schematic of a method of producing multiple protein products from a single lot of blood-based material.

FIG. 4 depicts a flow diagram similar to FIG. 3. However FIG. 4 includes additional processing of first and second precipitates, and first and second flow-throughs, which produces multiple products from a single lot of blood-based material. It should be appreciated that first precipitate can be dissolved and further processed by salt fractionation and/or chromatography processes as referred to in this document. As depicted, it is preferred that the product of second through sixth chromatography steps each is an isolated blood plasma protein as described herein. In some embodiments, the first through sixth chromatography steps are each different from each other. It is contemplated that first through fifth proteins are distinct blood plasma proteins from each other, though it may be that some protein batches at least partially contain the same protein.

Figure 5:
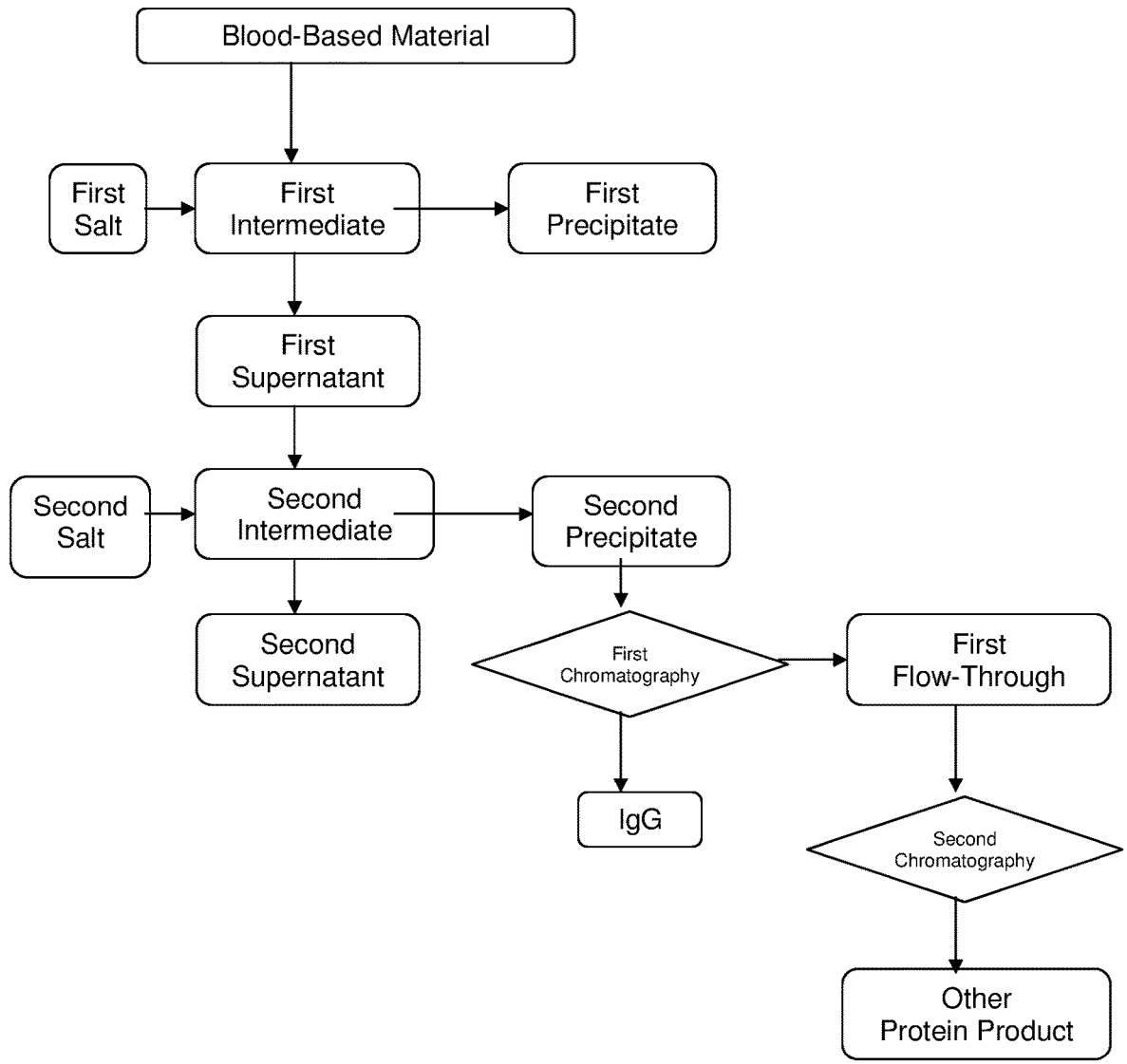
FIG. 5 is a schematic of a method of producing Immunoglobulin G and other protein products from a single lot of blood-based material.

FIG. 5 depicts a flow diagram for isolating Immunoglobulin G ("IgG") and other proteins from a single lot of blood-based material. The preparation of first and second intermediate can be the same or similar to the methods described above for FIGS. 1-4. As in the flow diagram of FIG. 4, the second precipitate is further processed by first chromatography step to produce IgG. While it is contemplated that first chromatography step comprises affinity chromatography by way of IgG specific affinity resin, it should be appreciated that first chromatography step can comprise, either wholly or in part, other types of chromatography as known in the art. In addition, first flow through is further processed by second chromatography step in order to produce other protein products, such as blood plasma proteins described herein. It should be appreciated that subsequent chromatography and salt fractionation steps can be performed to yield desired isolated protein products and combinations.

Figure 6:
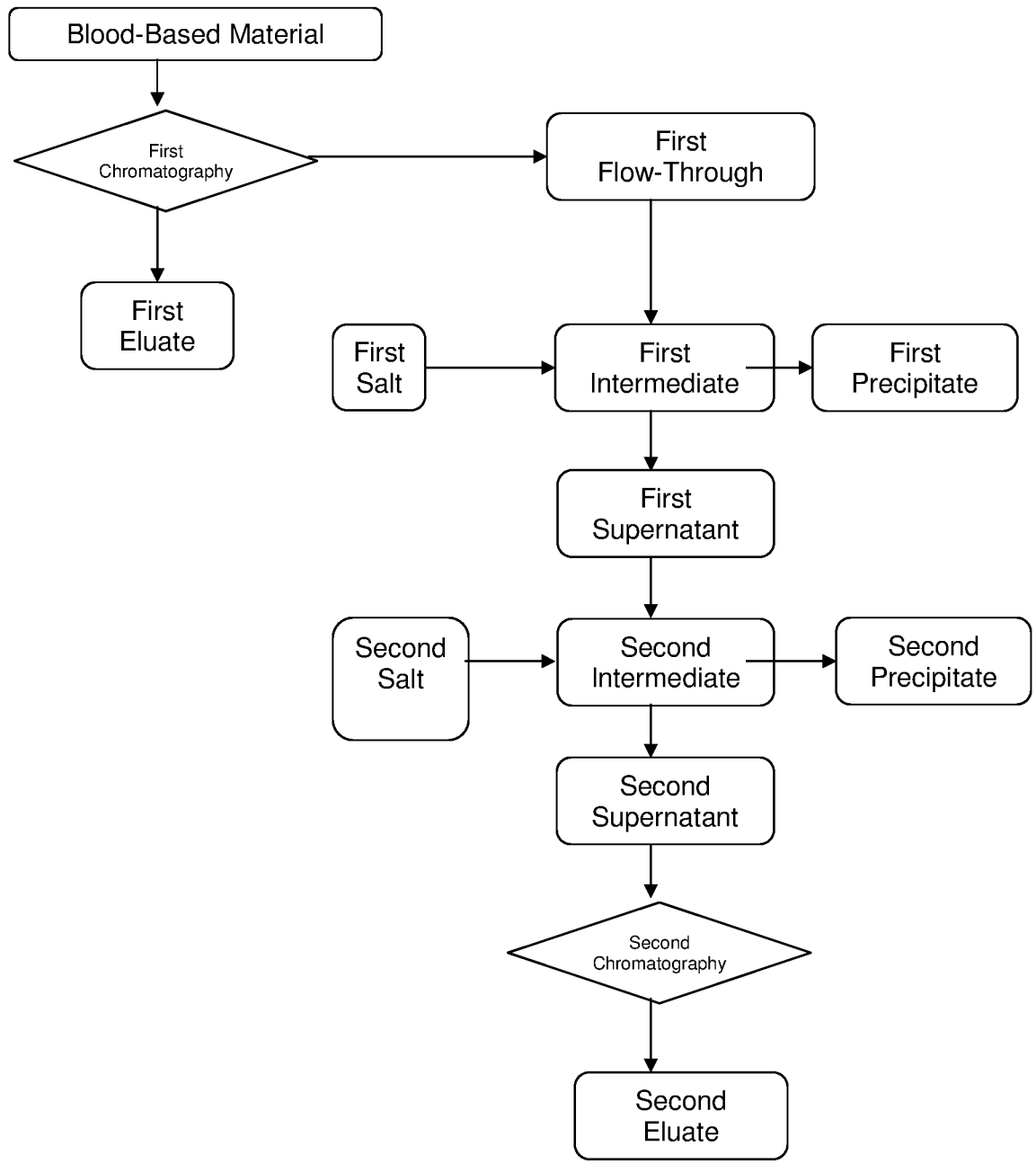
FIG. 6 is a schematic of another method of producing a protein product from a blood-based material.

FIG. 6 depicts a flow diagram for an alternate method of deriving desired products from blood-based material. The flow diagram of FIG. 6 begins with processing blood-based material via a first chromatography step. In some embodiments, the blood-based material is in-process material from other fractionation processes, or otherwise fractionated blood-based material. The first flow-through of FIG. 6 is then salt fractionated as described in FIGS. 1 and 3, and a second eluate produced by processing second supernatant with second chromatography step. It should be appreciated that first and second eluates comprise blood plasma proteins as described herein. In preferred embodiments, the second eluate comprises an isolated type of blood plasma protein.

Figure 7:
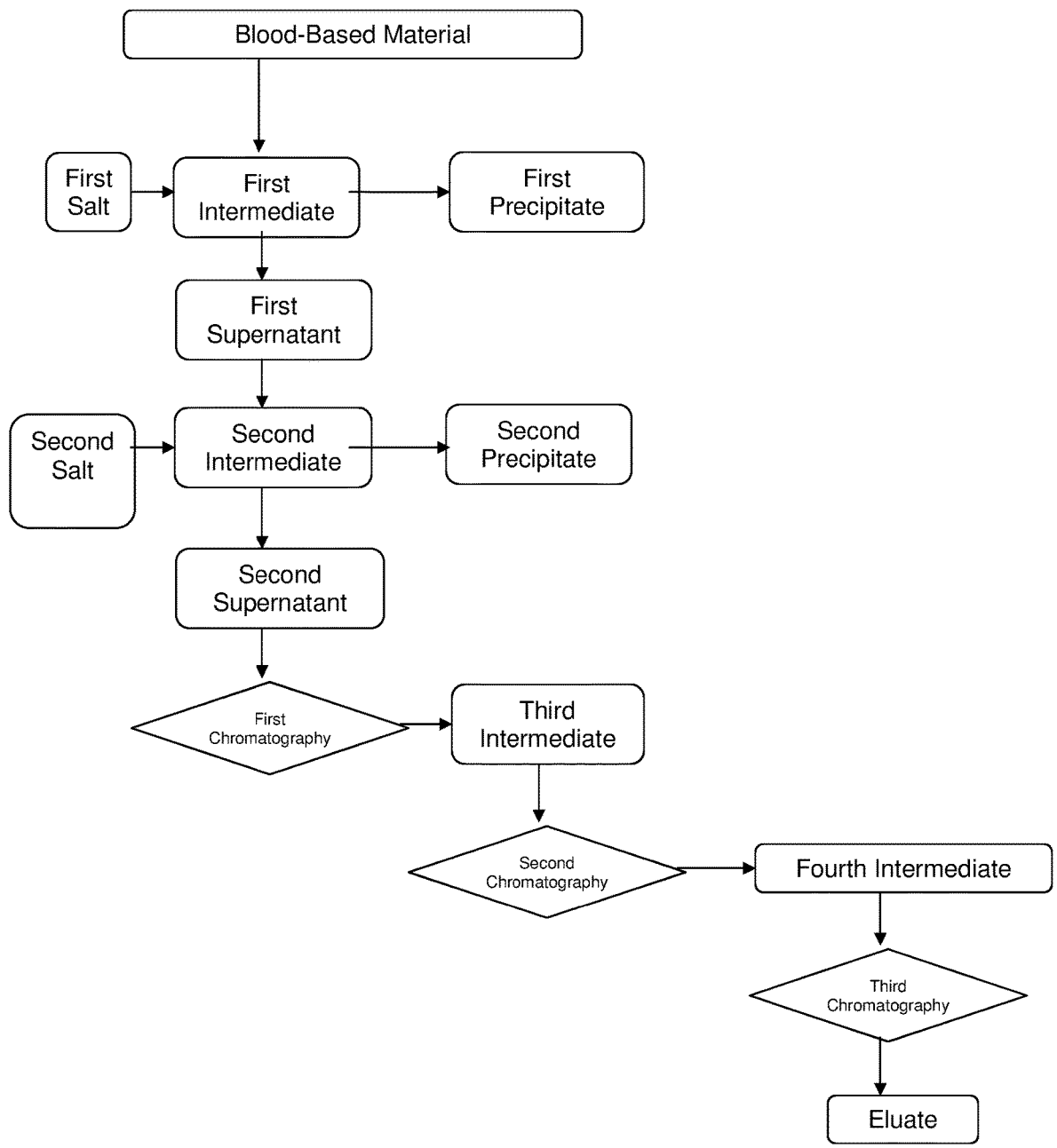
FIG. 7 is a schematic of another method of producing a protein product from a blood-based material.

FIG. 7 depicts a flow diagram similar to FIG. 3. However FIG. 7 discloses an embodiment comprising a third chromatography step. It should be appreciated that third chromatography step can comprise any of the chromatography steps previously discussed or known to the art. In some embodiments first through third chromatography steps comprise the same type of chromatography. Additional chromatography steps after or before the third chromatography step are also contemplated. In some embodiments, the eluate of the third chromatography step comprises at least one of the blood plasma proteins described herein. In some embodiments, the eluate comprises an isolated type of blood plasma protein.

Figure 8:
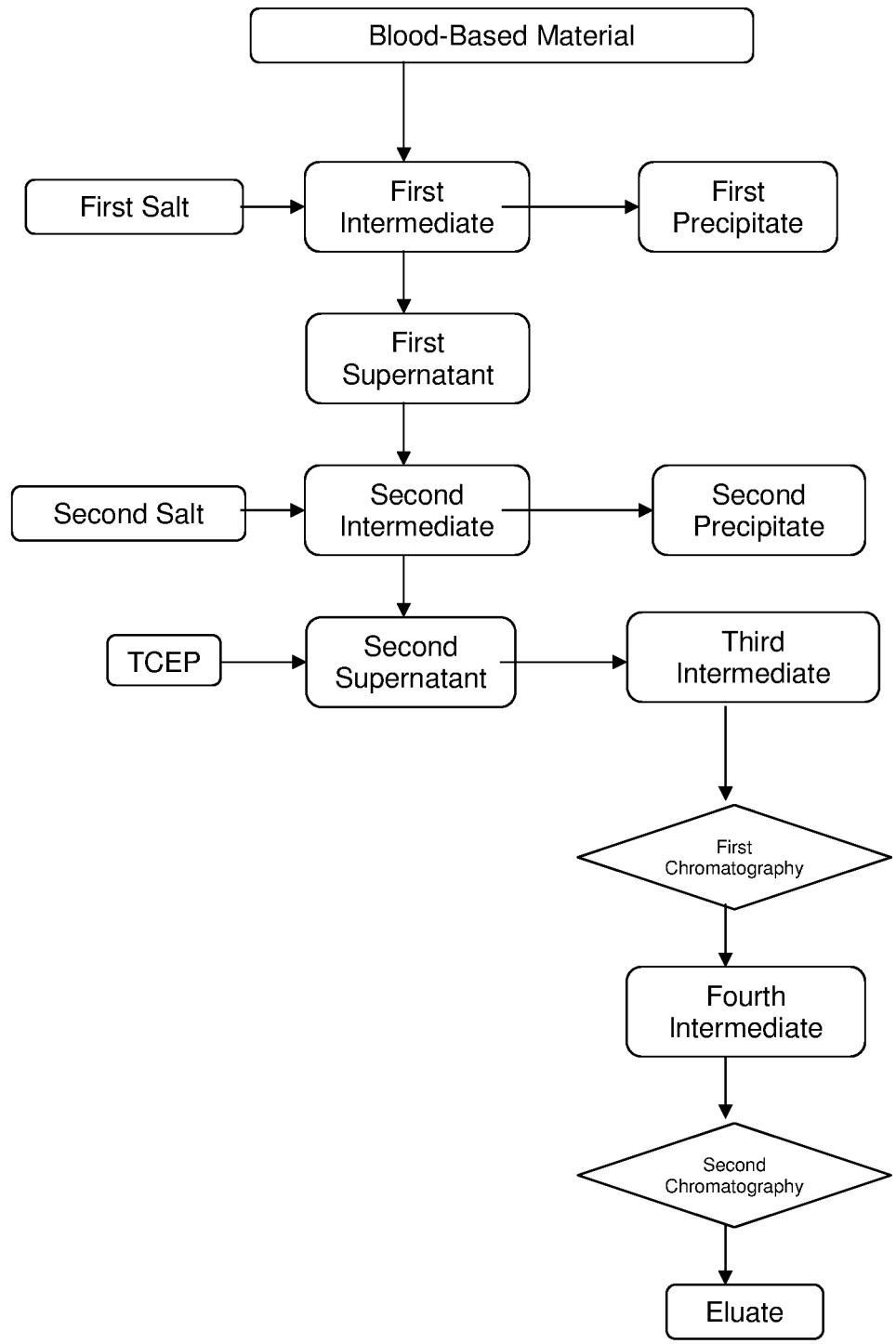
FIG. 8 is a schematic of another method of producing a protein product from a blood-based material.

FIG. 8 depicts a flow diagram similar to FIG. 3. However, FIG. 8 comprises an additional step of adding TCEP to the second supernatant to produce third intermediate. It is contemplated that TCEP reduces the multimer formation of at least some proteins in the second supernatant. It is also contemplated that additional or alternative reducing agents may be used to minimize multimer formation of proteins throughout the steps of FIG. 8. (e.g., DTT and βME). In some embodiments, the eluate of the second chromatography step comprises at least one of the blood plasma proteins described herein. In some embodiments, the eluate comprises an isolated type of blood plasma protein.

Figure 9:
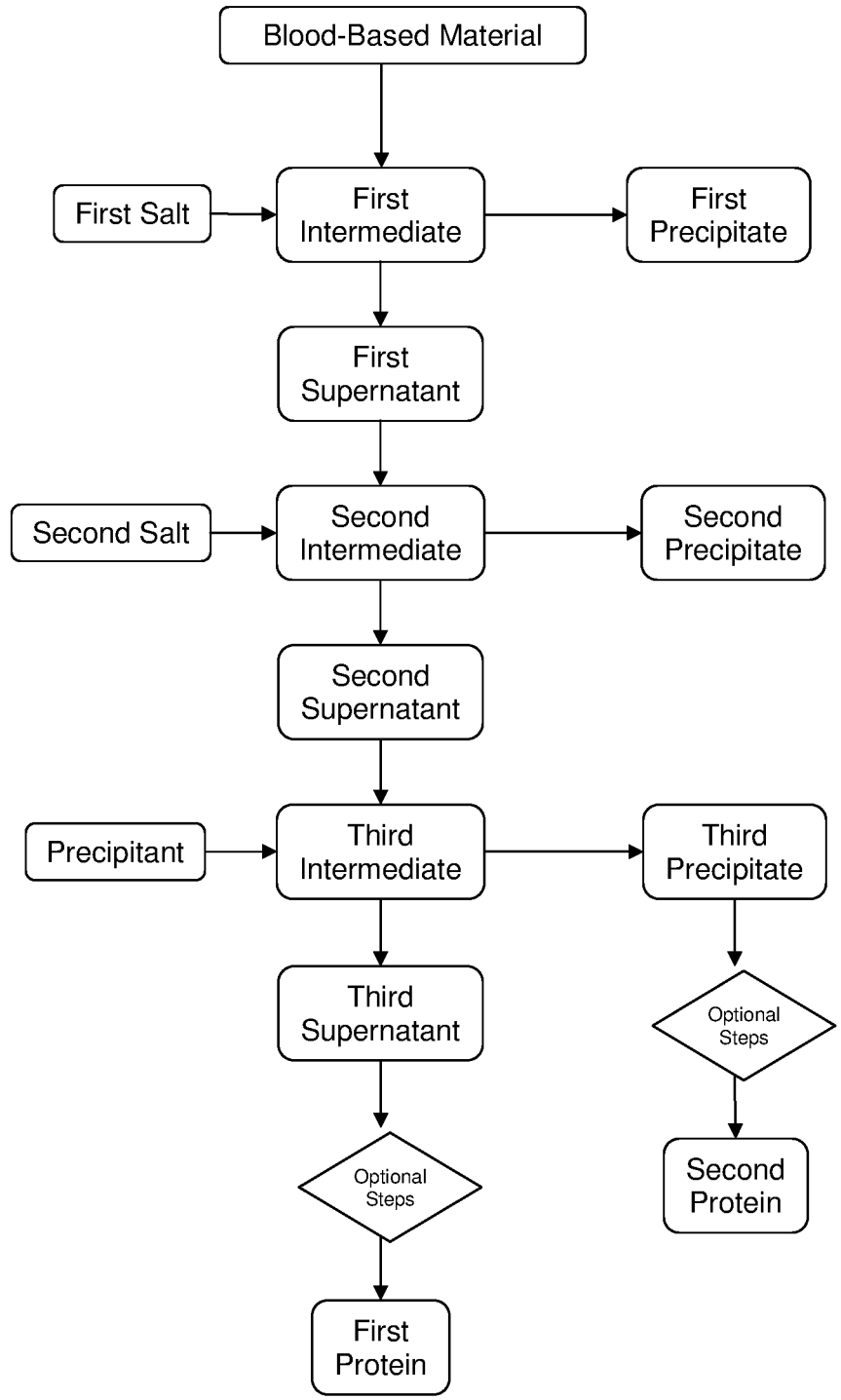
FIG. 9 is a schematic of another method of producing a protein product from a blood-based material.

FIG. 9 depicts another flow diagram similar to FIG. 3. In FIG. 8, an additional precipitation step is performed by adding a precipitant to the second supernatant to produce a third intermediate. The precipitant may comprise the first or second salt (e.g., citrates, acetates, and gluconates), a different salt (e.g., sodium chloride, ammonium sulfate, a caprylate salt, etc.), a polyethylene glycol, an alcohol, or another precipitant. The third intermediate can then be separated to produce a third supernatant and a third precipitate by centrifugation and/or filtration. The third supernatant and third precipitate may each be subjected to optional purification steps (e.g., chromatography, solvent/detergent treatment, bioburden filtration, and/or concentration step(s), as described above) to produce first and second proteins, respectively. It should be appreciated that multiple protein products may be purified from either or both of the third supernatant and third precipitate.

Example

Human plasma was subjected to sequential 12% citrate and 22% citrate protein precipitation steps as described in U.S. Pat. No. 7,879,331. The citrate concentration of the supernatant resulting from fractionation at 22% citrate was increased in separate studies to 26%, 30% or 34%. The resulting intermediate was chilled to below 5° C. with stirring, and stirred at this temperature for 60 minutes. The precipitate was separated by centrifugation (as described in U.S. Pat. No. 7,879,331) and the fractions analyzed by nephelometry for alpha-1-proteinase inhibitor (A1PI), albumin, and total protein. The results are presented in the Table 1. The values are the percentages found in each of the supernatant (super) and the precipitate (ppt), normalized to 100% (sum of supernatant and precipitate).

TABLE 1

| Sample | A1PI | Total protein | Albumin |
| --- | --- | --- | --- |
| 26% Cit super | 99 | 94 | 98 |
| 26% Cit ppt | BDL | 6 | 2 |
| 30% Cit super | 97 | 89 | 96 |
| 30% Cit ppt | 3 | 10 | 4 |
| 34% Cit super | 97 | 92 | 97 |
| 34% Cit ppt | 3 | 8 | 3 |

Advantageously, increasing citrate concentration removed additional proteins from the resulting supernatant while only a small fraction of the alpha-1-proteinase inhibitor and albumin were precipitated. Therefore, performing a third precipitation step may be useful in removing non-product proteins from the resulting supernatant while losing only a small fraction of the protein product(s). In yet further aspects of the inventive subject matter, processes for producing products from blood-based materials can comprise first and second modules. Each module is configured to receive an input material and to yield at least one output material. The first and second modules can each comprise a fractionation module, a chromatography module, a filtration module, a separation module, or a sterilization module. The input of one module can comprise the output of another module.

Figure 10:
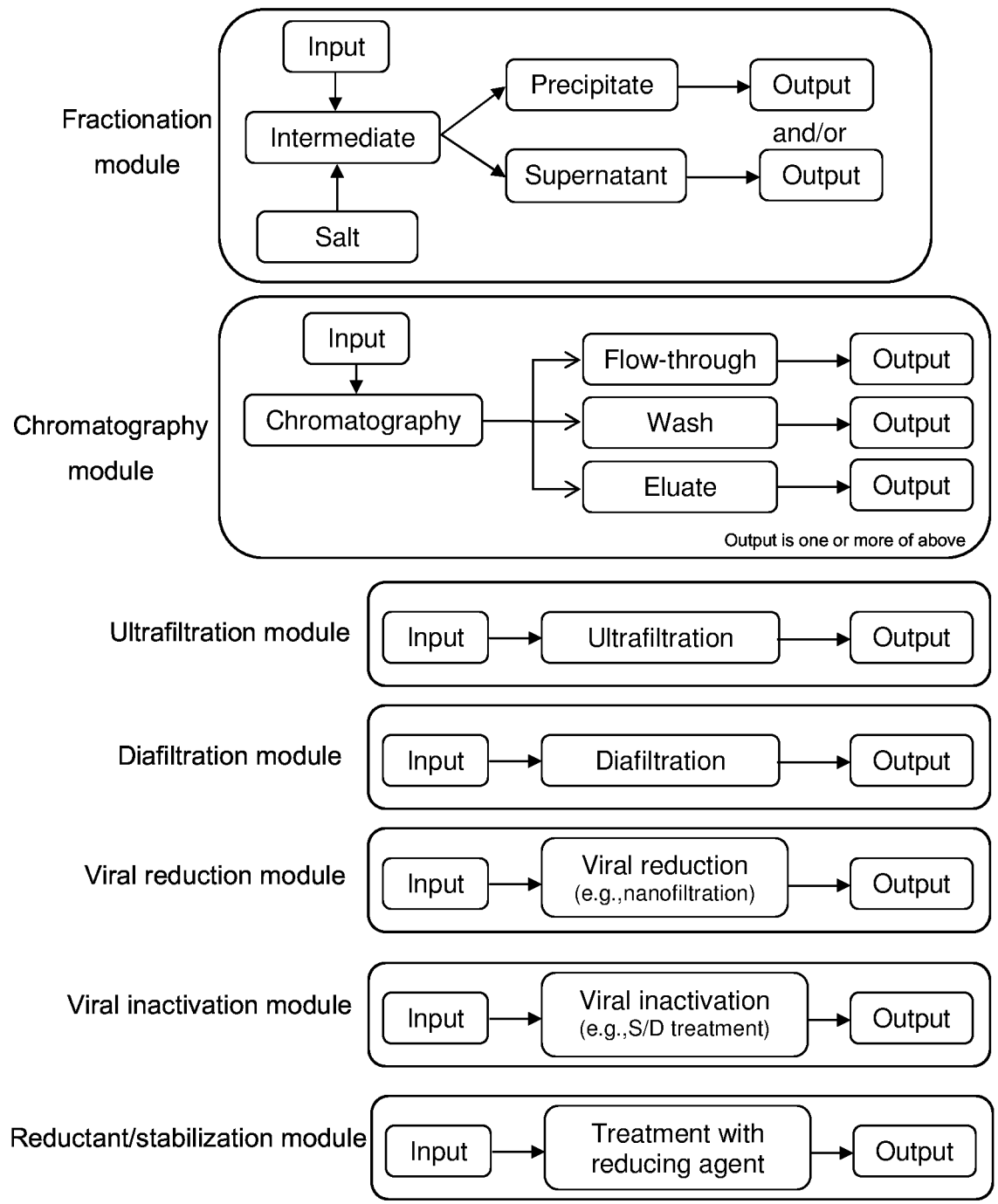
FIG. 10 is a schematic of exemplary processes modules for producing protein products.

FIG. 10 depicts several modules contemplated by the inventive subject matter. In fractionation modules, the input material is fractionated by salt fractionation, Cohn fractionation, or Nitschmann and Kistler fractions, caprylate fractions or variations thereof. Salt is added to the input material, creating an intermediate. When a module employs a salt fractionation step as discussed herein, the output material comprises at least a supernatant and a paste or precipitate.

In regard to chromatography modules, input material is separated into a flow-through a wash, and one or more eluates by chromatography processes. Suitable chromatography processes include affinity chromatography, gel permeation, cation exchange, anion exchange, hydrophobic interaction, hydroxyapatite, fluoroapatite, expanded bed absorption, or immobilized metal ion affinity chromatography. The output material of the chromatography modules comprises at least a flow-through and an eluate, and can include a wash.

Ultrafiltration and diafiltration modules are also contemplated. It should be appreciated that diafiltration or ultrafiltration modules are suitable filtration methods for desalting and concentrating input materials, respectively. Additionally, viral reduction modules (e.g., via nanofiltration or otherwise described herein) and viral inactivation modules (e.g., via solvent/detergent treatment or otherwise described herein) are also contemplated. Further, reductant/stabilization modules (e.g., via treatment with TCEP, DTT, βME, or other suitable reducing agents) are contemplated by the inventive subject matter.

The sequence of modules can be configured to produce a variety of products from blood-based material. With respect to the number of modules employed in the inventive processes, the inventors contemplate that the number of modules required depends on the number of modular process steps required to produce the desired product. Some embodiments comprise one or two modules. Preferred methods of the inventive subject matter include three, four, five, six, seven, eight, nine, ten or more modules.

Figure 11:
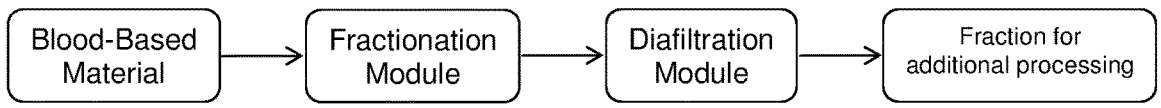
FIG. 11 is a schematic of three exemplary modular processes for producing protein products.
Figure 11:
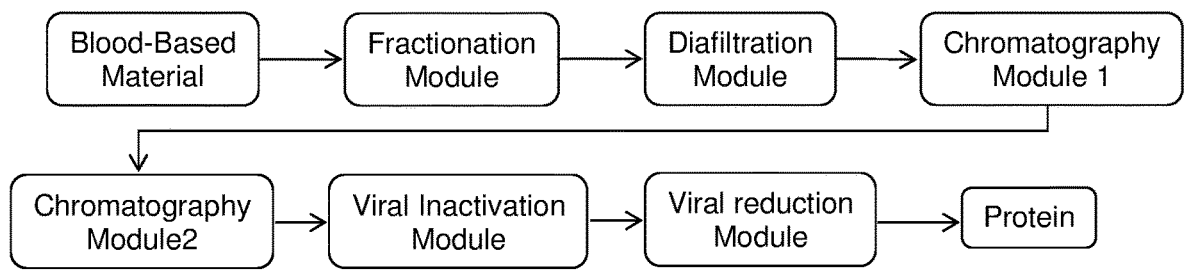
Figure 11:
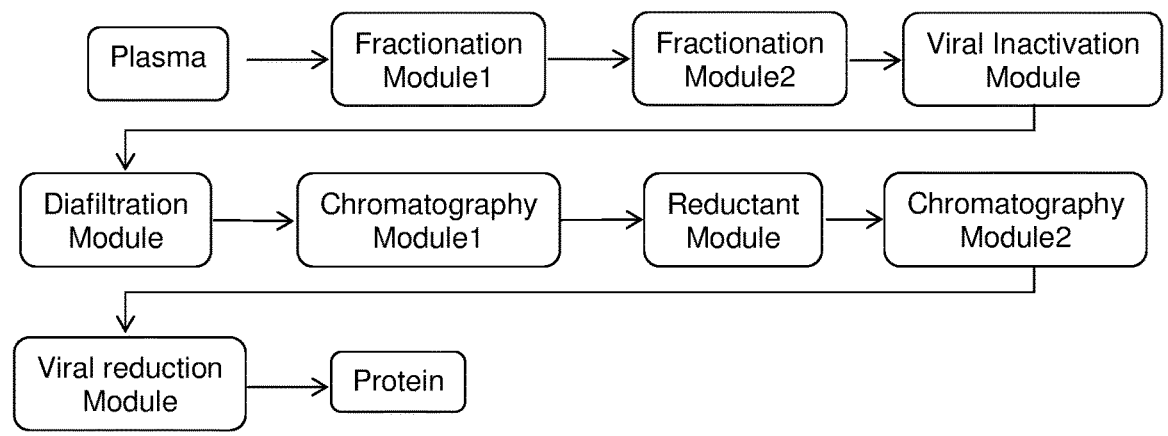

FIG. 11 depicts a number of sample modular processes of the inventive subject matter that employ the modules of FIG. 10. It should be appreciated that the output from one module is used as the input of another module. As depicted in process A of FIG. 11, blood-based material is used as the input material of a fractionation module. At least one of the outputs of the fractionation module (supernatant and paste) is used as the input material for a diafiltration module. The output of the diafiltration module is then further used as input material in downstream processes.

Process B of FIG. 11 uses blood-based material as the input material in a fractionation module. At least one of the outputs of the fractionation module (supernatant and paste)

is used as the input material for a diafiltration module. The output of the diafiltration module is then used as input material in chromatography module 1. At least one of the outputs of chromatography module 1 (flow-through, wash, and eluate) are used as an input material in chromatography module 2. It should be appreciated that chromatography modules 1 and 2 can be the same type of chromatography or can be different types of chromatography. At least one of the outputs of chromatography module 2 are used as an input material in a viral inactivation module. The output of the viral inactivation module is used as the input material in a viral reduction module. The output of the viral reduction module comprises a blood-based protein (e.g., at least one of alpha-1-proteinase inhibitor, gamma globulin, immunoglobulin, albumin, factor VIII, factor IX, factor XIII, protein C, antithrombin III, fibrinogen, and C1 esterase inhibitor).

Process C of FIG. 11 uses plasma as the input material in fractionation module 1. At least one of the outputs of fractionation module 1 (supernatant and paste) is used as the input material for fractionation module 2. It should be appreciated that fractionation modules 1 and 2 can be the same type of fractionation or can be different types of fractionation. At least one of the outputs of fractionation module 2 is used as the input material for a viral inactivation module. The output of the viral inactivation module is used as the input material of a diafiltration module. The output of the diafiltration module is then used as input material in chromatography module 1. At least one of the outputs of chromatography module 1 (flow-through, wash, and eluate) are used as an input material in a reductant module. The output of the reductant module is then used as the input material of chromatography module 2. It should be appreciated that chromatography modules 1 and 2 can be the same type of chromatography or can be different types of chromatography. At least one of the outputs of chromatography module 2 is used as an input material in a viral reduction module. The output of the viral reduction module comprises a blood-based protein (e.g., at least one of alpha-1-proteinase inhibitor, gamma globulin, immunoglobulin, albumin, factor VIII, factor IX, factor XIII, protein C, antithrombin III, fibrinogen, and C1 esterase inhibitor).

It is further contemplated that the input material for the first module can comprise at least one of a blood-based material and an output material from any other module, e.g., a flow-through, an eluate, a supernatant, a paste, or a dissolved paste. Recycling of output materials from one module back into the same module is not excluded.

The numbers expressing quantities of ingredients, properties such as concentration, reaction conditions, and so forth, used to describe and claim certain embodiments of the invention are to be understood as being modified in some instances by the term "about." Accordingly the numerical parameters set forth in the written description and attached claims are approximations that can vary depending upon the desired properties sought to be obtained by a particular embodiment. The numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

The discussion herein provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

What is claimed is:

1. A method of producing an immunoglobulin G product from a blood-based material, the method comprising:
    applying the blood-based material to a first fractionation module, wherein a first salt is added to the blood-based material to produce a first intermediate, wherein the salt comprises between 11-20 wt % of the first intermediate;

and wherein the first intermediate is separated to produce a first supernatant and a first paste;

transferring the first supernatant to a second fractionation module, wherein a second salt is added to the first supernatant to produce a second intermediate, wherein the second salt comprises between 15-30 wt % of the second intermediate; and wherein the second intermediate is separated to produce a second supernatant and a second paste;

dissolving the second paste to generate a dissolved second paste;

transferring the dissolved second paste to a viral inactivation module and applying a virus inactivating agent to the dissolved second paste to generate a treated dissolved second paste; and transferring the treated dissolved second paste to a first chromatography module wherein the treated dissolved second paste is separated by a first chromatography process comprising an anion exchange resin to produce a first flow-through and a first eluate, wherein the first flowthrough comprises immunoglobulin G.

2. The method of claim 1, wherein the first salt comprises at least one of a citrate, an acetate, and a gluconate.

3. The method of claim 1, wherein the first salt is the same as the second salt.

4. The method of claim 1, wherein the dissolved second paste is transferred to a diafiltration or ultrafiltration module.

5. The method of claim 1, further comprising isolating an additional protein product from at least one of the first paste, the second supernatant, and the first eluate.

6. The method of claim 1, comprising applying the first flow-through to a second chromatography module comprising an ion exchange resin, wherein the first flow-through is separated into a second flow-though and a second eluate, wherein the ion exchange resin is the anion exchange resin, and wherein the second flow-through comprises immunoglobulin G.

* * * * *